(12) United States Patent
Chen et al.

(10) Patent No.: US 8,086,415 B2
(45) Date of Patent: Dec. 27, 2011

(54) MOLECULARLY IMPRINTED POLYMER

(75) Inventors: Beining Chen, Cranfield (GB); Richard Michael Day, Navestock (GB); Sreenath Subrahmanyam, Madras (IN); Sergiy Anatoliyovich Piletsky, Cranfield (GB); Olena Volodimirivna Piletska, Cranfield (GB); Anthony Peter Francis Turner, North Crawley (GB)

(73) Assignee: Cranfield University, Milton Keynes (GB)

( * ) Notice: Subject to any disclaimer, the term of this patent is extended or adjusted under 35 U.S.C. 154(b) by 839 days.

(21) Appl. No.: 11/933,913

(22) Filed: Nov. 1, 2007

(65) Prior Publication Data

US 2008/0214405 A1 Sep. 4, 2008

Related U.S. Application Data

(62) Division of application No. 10/181,435, filed as application No. PCT/GB01/00324 on Jan. 25, 2001, now abandoned.

(30) Foreign Application Priority Data

Jan. 25, 2000 (GB) .................................. 0001513.1

(51) Int. Cl.
*G01N 31/00* (2006.01)
(52) U.S. Cl. ........................................................ 702/22
(58) Field of Classification Search .................... 702/22
See application file for complete search history.

(56) References Cited

U.S. PATENT DOCUMENTS 6,253,168 B1 6/2001 Griffey et al.

FOREIGN PATENT DOCUMENTS

| EP | 0818744 | 1/1998 |
|---|---|---|
| WO | 93 09075 | 5/1993 |

OTHER PUBLICATIONS

Rogan et al., "Synergistic Use of Virtual Screening and Biophysical Methods for the Protein-Based Design of Peptidomimetics," Chimia (2000) vol. 54, pp. 658-662.*
Pande et al., "Phase Diagram of Heteropolymers with an Imprinted Conformation," Macromolecules (1995) vol. 28, pp. 2218-2227.*
Takeuchi et al., "Molecular Imprinting: An Approach to "Tailor-Made" Synthetic Polymers with Biomimetic Functions," Acta Polymer (1996) vol. 47, pp. 471-480.*
Kempe et al. Journal of Molecular Recognition. 1993. vol. 6, on.1, pp. 25-29, abstract only.
Mosbach et al. Bio/Technology. (1996) vol. 14, pp. 163-170, abstract only.
Jin Cho Sung et al.: "Rational combinatiorial library desing. 2. Rational design of targeted combinatorial peptide libraries using chemical similarity probe and inverse QSAR approaches" J. Chem. Inf. Comput. Sci., vol. 38, No. 2 pp. 251-268 Apr. 3, 1998.
Zheng Weifan et al.: "Rational combinatiorial library desing. 1. Focus-2D: A new approach to the design of targeted combinatorial chemical libraries" J. Chem. Inf. Comput. Sci., vol. 38, No. 2 pp. 251-258 Apr. 3, 1998.
Takeuchi Toshifumi et al.: "Combinatorial molecular imprinting: an approache to synthetic polymer receptors" Anal. Chem., vol. 71, No. 2, pp. 285-290 Nov. 12, 1998.

* cited by examiner

*Primary Examiner* — Jerry Lin
(74) *Attorney, Agent, or Firm* — Oblon, Spivak, McClelland, Maier & Neustadt, L.L.P.

(57) ABSTRACT

A computer aided rational molecular design method that includes establishing a virtual library of functional monomers each having a portion that is capable of polymerizing and a functional group that is capable of interacting with a template molecule with the aid of a computer, designing a molecular model of a biological template molecule by a computer facilitated molecular mechanical method and screening said virtual library of functional monomers and selecting those monomers which have the highest binding score to the template molecule by their functional group.

8 Claims, 8 Drawing Sheets

(a) Itaconic acid (−37.05 kCal Mol⁻¹)

(b) Acrylamide (−35.78 kCal Mol⁻¹)

(c) 2-Acryl-2-methyl-1-propane sulphonic acid (−32.64 kCal Mol⁻¹)

(d) N`N Methylbisacrylate (−31.63 kCal Mol⁻¹)

(e) Acrylic Acid (−29.61 kCal Mol⁻¹)

MOLECULARLY IMPRINTED POLYMER

This application is a Divisional application of Ser. No. 10/181,435, pending.

TECHNICAL FIELD

The present invention relates to methods and means for use in the preparation of molecularly imprinted polymers ("MIPs"), to the MIPs that can be created using them, and to applications of the MIPs.

The present invention particularly relates to an application of computer-aided rational design techniques for the rapid development and optimization of polymers that act as synthetic receptors. Specifically the imprinted polymers are synthesized by a polymerization of individual monomers with or without cross-linker in the presence of template molecule(s), which can be small molecules such as drugs, pesticides, peptides as well as large molecules such as carbohydrates, nucleic acids and proteins.

BACKGROUND ART

Molecularly imprinted polymers (MIPs), materials with artificially created receptor-like recognition properties, have recently attracted significant attention as potential substitutes for unstable receptors and antibodies in affinity chromatography, membranes, capillary electrophoresis and sensor technology (U.S. Pat. Nos. 5,110,833, 5,587,273, 5,756,717, 5,728,296, 5,786,428 and 5,849,215). Among the factors limiting their practical application is the absence of a general procedure for polymer synthesis. Several attempts have been made to develop a general procedure for rational design of the imprinted polymers (Nicholls I. A. (1995): Thermodynamic consideration for the design of and ligand recognition by molecularly imprinted polymers, *Chem. Lett.*, 1035-1036; Whitcombe M. J., Martin L., Vulfson E. N. (1998): Predicting the selectivity of imprinted polymers. *Chromatography*, 47, 457-464; Takeuchi T., Fukuma D., Matsui J. (1999): Combinatorial molecular imprinting: an approach to synthetic polymer receptors. *Anal. Chem.*, 71, 285-290). In the best cases they give rules or hints, indicating how the MIP should be made in order to possess a certain level of specificity. Thus it is recommended that the polymerization should be performed in a hydrophobic solvent in order to produce a material able to interact with the template through electrostatic interactions. At the same time the choice of monomers, solvent and polymerization conditions in most cases depends on general principles, personal experience or information about similar systems. In some extreme cases it has been necessary to produce and investigate hundreds of polymers in order to optimize MIP monomer composition (Takeuchi et al. op. cit).

DISCLOSURE OF INVENTION

The present invention describes a new method for rational choice of the functional monomers for the preparation of MIPs.

The present invention describes a computer-aided rational design techniques for the rapid development and optimization of molecularly imprinted polymers, which includes screening of a virtual library of functional monomers for their interaction with the template molecule and selection of those monomers forming a strong complex with the template for polymer preparation. The procedure of monomer selection includes several stages (it is important to note that each individual step as well as their combination can be used separately for the design of MIPs and are covered by the present invention). First, a virtual library of molecular models of functional monomers is produced containing molecules that possess polymerizable residues and residues able to interact with a template, e.g. through electrostatic, hydrophobic van-der-Waals forces, dipole-dipole interactions and/or reversible covalent bonds. Secondly, a molecular model of the template molecule is prepared. Charges for each atom are calculated, and the structure of the template and monomers refined using molecular mechanical methods. Thirdly, each of the entries in the virtual library is probed for their possible interaction with the template molecule. The monomers giving the highest binding score represent the best candidates for polymer preparation. Fourthly, copies of the most ideal hits are placed around the target. Simulated annealing is then used to simulate pre-arrangement of the functional monomers with template in the monomer mixture prior to polymerization. At the end of the program, the number and the position of the functional monomers are examined The type and quantity of the monomers participating in the complex with template indicate the type and ratio of the template and monomers in an optimized MIP composition. Finally a mixture of monomers corresponding to this composition is polymerised in the presence of the template to produce a MIP.

Main embodiments include:

1. A computer-aided rational design technique for the rapid development and optimization of molecularly imprinted polymers (MIPs), which includes design of a virtual library of functional monomers and screening of their interaction with a template molecule. Functional monomers should possess polymerizable residues and residues able to interact with the template, e.g. through electrostatic, hydrophobic van-der-Waals forces, dipole-dipole interactions and/or reversible covalent bonds. The library of functional monomers may include one or more of vinyl monomers, allyl monomers, acetylenes, acrylates, methacrylates, amino acids, nucleosides, nucleotides, carbohydrates, phenols, heterocycles, aniline, and their derivatives.

2. Design of a molecular model of the template using molecular mechanical methods. The template molecule may be selected from biological receptors, nucleic acids, hormones, heparin, antibiotics, vitamins, drugs, cell components and components of viruses such as carbohydrates, saccharides, nucleoproteins, mucoproteins, lipoproteins, peptides and proteins, glycoproteins, glucosaminoglycanes and steroids.

3. Screening of the virtual library of the functional monomers for their ability to form molecular complex with the template. The monomers giving the highest binding score represent the best candidates for polymer preparation.

4. Placing of the functional monomers (or monomers giving the highest binding score) around the template and using molecular mechanics in order to simulate pre-arrangement of the functional monomers with template in the monomer mixture prior to polymerization. At the end of the program, the number and the position of the functional monomers are examined The type and quantity of the monomers participating in the complex with template indicate the type and ratio of the template and monomers in an optimized MIP composition.

5. The parameters of the modeling and screening (dielectric constants, temperature chosen for "annealing" procedure, type of interactions) could be modified in order to simulate the real polymerization or re-binding conditions.

MODES FOR CARRYING OUT THE INVENTION

The first embodiment describes the design of a virtual library of functional monomers which possess polymerizable residues and residues, able to interact with a template through electrostatic, hydrophobic van-der-Waals forces, dipole-dipole interactions or reversible covalent bonds. The library of functional monomers should contain at least two, and preferably more monomers which can be vinyl monomers, allyl monomers, acetylenes, acrylates, methacrylates, amino acids, nucleosides, nucleotides, sugars and saccharides, carbohydrates, phenols, heterocycles, aniline, and their derivatives. Preferable monomers are these able to interact with the template through non-covalent interactions and be polymerized through a radical mechanism.

The second embodiment describes the design of a molecular model of the template using molecular mechanical methods. The template is selected from a group including biological receptors, nucleic acids, immunosuppressants, hormones, heparin, antibiotics, vitamins, drugs, cell components and components of viruses such as carbohydrates, lipids, saccharides, nucleoproteins, mucoproteins, lipoproteins, peptides and proteins, glycoproteins, glucosaminoglycanes and steroids.

The third embodiment describes screening the virtual library of functional monomers for their ability to form a molecular complex with the template. The monomers giving the highest binding score represent the best candidates for polymer preparation and can be used directly for the polymer synthesis as part of a monomer mixture.

The fourth embodiment describes a refining step for optimizing the monomer composition. It includes placing of one or more functional monomers, preferably the monomers giving the highest binding score around the template, and using molecular mechanics to simulate pre-arrangement of the functional monomers with template in the monomer mixture prior to polymerization. At the end of the program, the number and the position of the functional monomers are examined. The refining step has three goals: first, to evaluate the quantity of the monomer units which should be used in complexation with template; second, to determine if cocktails of monomers form a stronger complex with the template than individual monomers; third, to check possible interactions between the functional monomers in a monomer mixture, both positive (stabilizing complex) and negative (competing). The type and quantity of the monomers participating in the complex with template (first shell layer), or their combination with the monomers which interact with the first shell layer of monomers, stabilizing complex (second shell layer) indicate the type and ratio of the template and monomers in an optimized MIP composition. All components of the refining process can be used and accounted for individually or in combination in the optimization of the monomer composition.

The sixth embodiment describes "fitting" of the modeling and screening parameters (dielectric constants, temperature chosen for "annealing" procedure, type of interactions) to real polymerization or re-binding conditions. If, for example, the template is not soluble in organic solvents then the dielectric constant could be changed from vacuum to water or the constant of the solvent used for polymerization. The temperature in the "annealing" procedure can be also adjusted to the one applied during polymerization or the re-binding step.

The present invention will now be further described in detail by reference to the following, examples, which are intended to illustrate some of the possibilities, but are in no way intended to limit the scope of the invention.

EXAMPLE 1

Figure 1A:
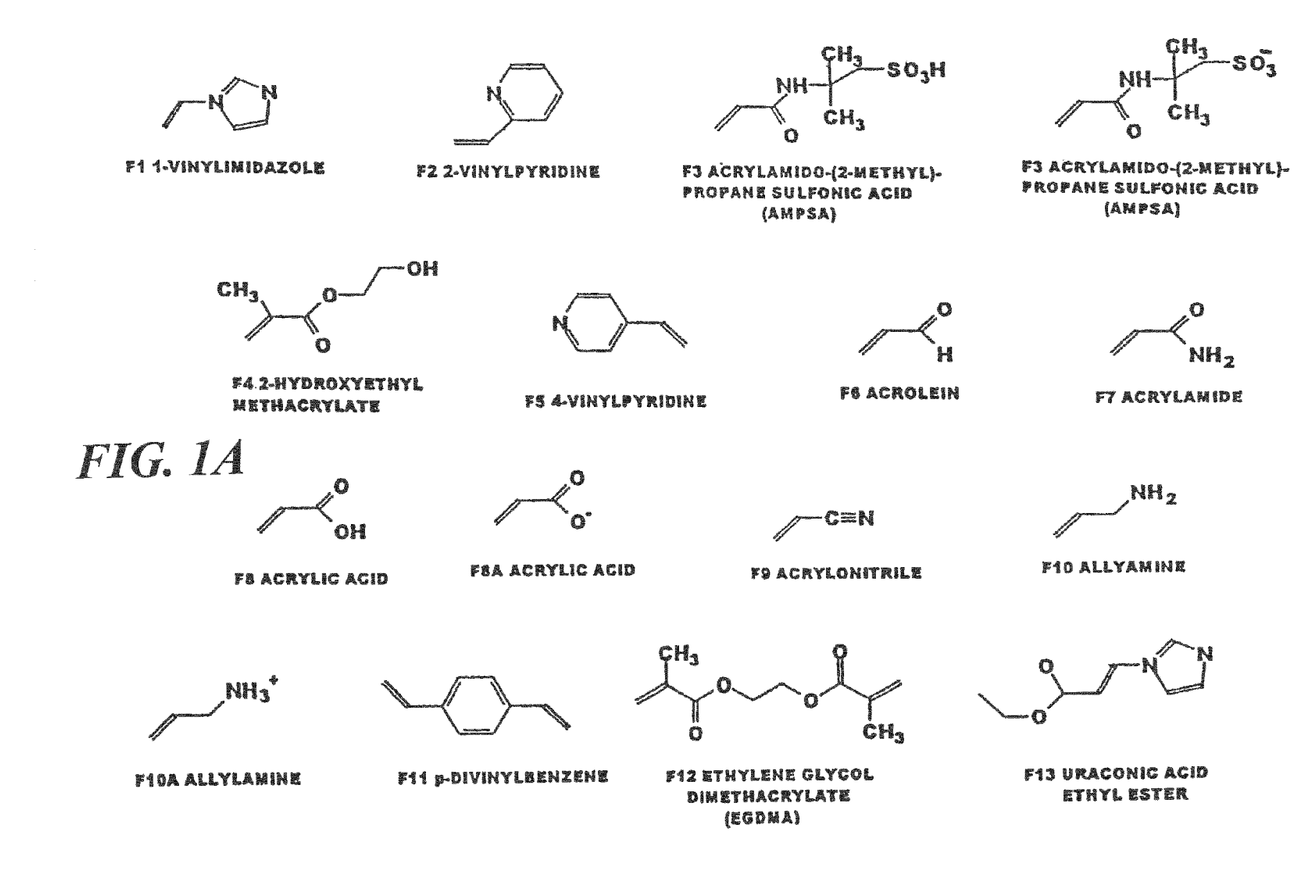
FIG. 1. Depicts a virtual library of the functional monomers used for the development of MIP, specific for atrazine.
Figure 1B:
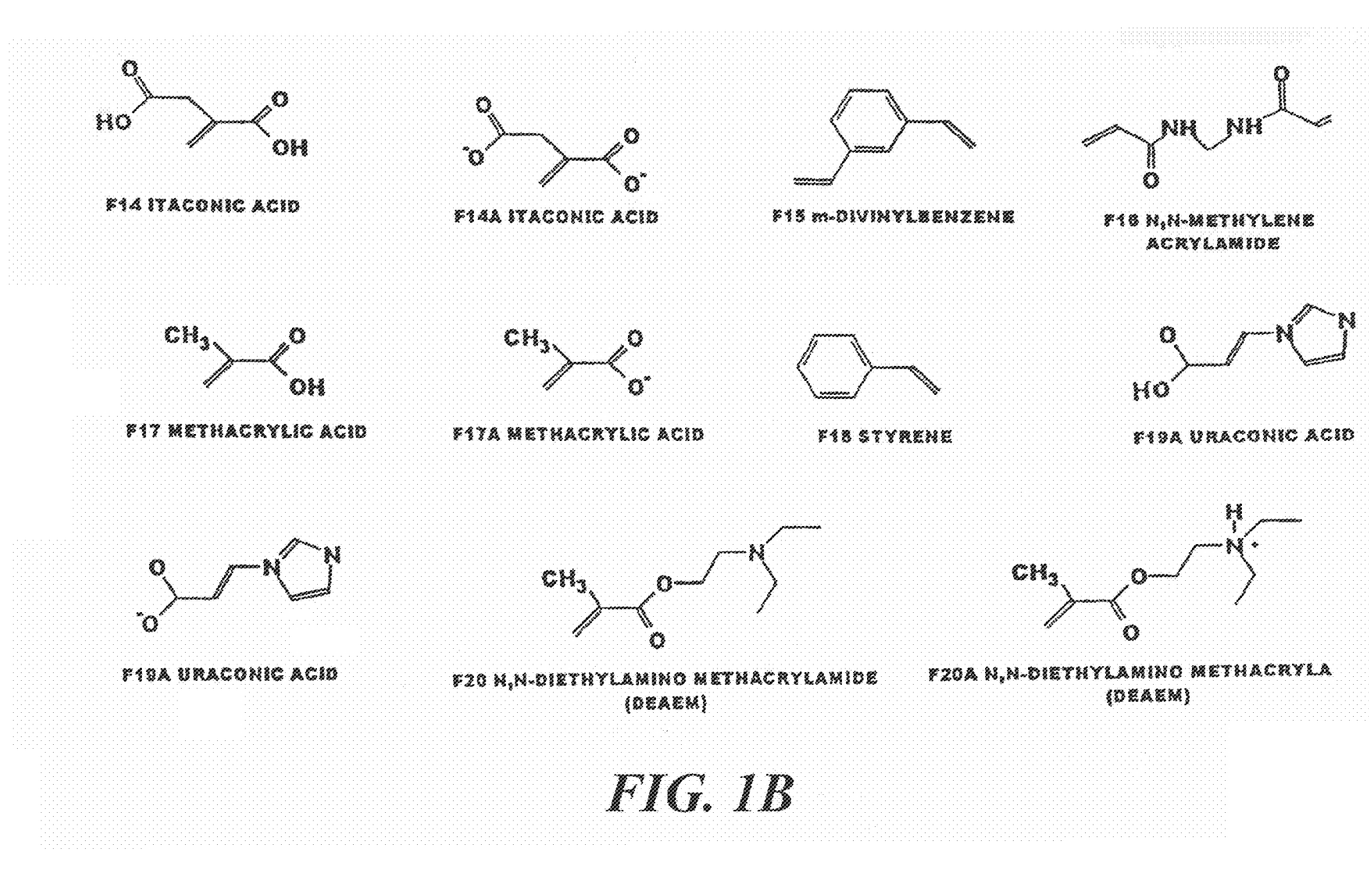

Computer Aided Design of an MIP Specific for Atrazine a) The workstation used to generate molecular models and perform simulation was a Silicon Graphics Octane running the IRIX 6.4 operating system. The workstation was configured with two 195 MHz reduced instruction set processors, 712 MB memory and a 12 Gb fixed drive. The system was used to execute the software packages SYBYL (Tripos). The virtual library contained the most frequently used functional monomers able to form non-covalent interactions with the template atrazine. These are methacrylic acid, acrylic acid, itaconic acid, acrolein, acrylamido-(2-methyl)-propane sulfonic acid (AMPSA), 2-vinylpyridine, 4-vinylpyridine, 1-vinylimidazole allylamine, N,N'-diethyl aminoethyl methacrylamide (DEAEM), acrylonitrile, 2-hydroxyethyl methacrylate, p-divinylbenzene, m-divinylbenzene, urocanic acid, urocanic ethyl ester, ethylene glycol dimethacrylate, N,N'-methylene-bis-acrylamide, styrene, acrylamide and, where appropriate, their protonated or deprotonated forms (see FIG. 1).

Figure 2:
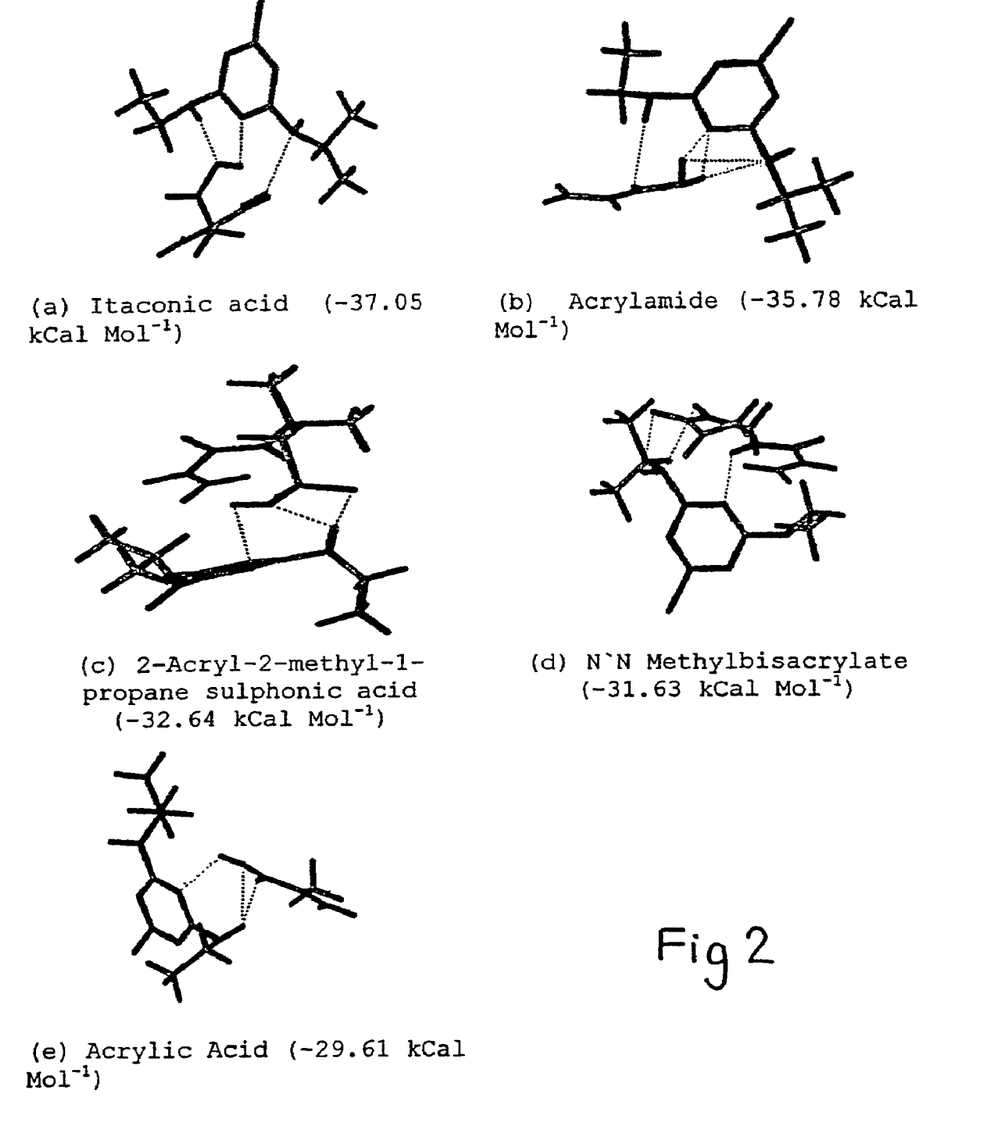
FIG. 2. Shows the functional monomers from the virtual library giving the highest binding score when interacting with atrazine.
Figure 3:
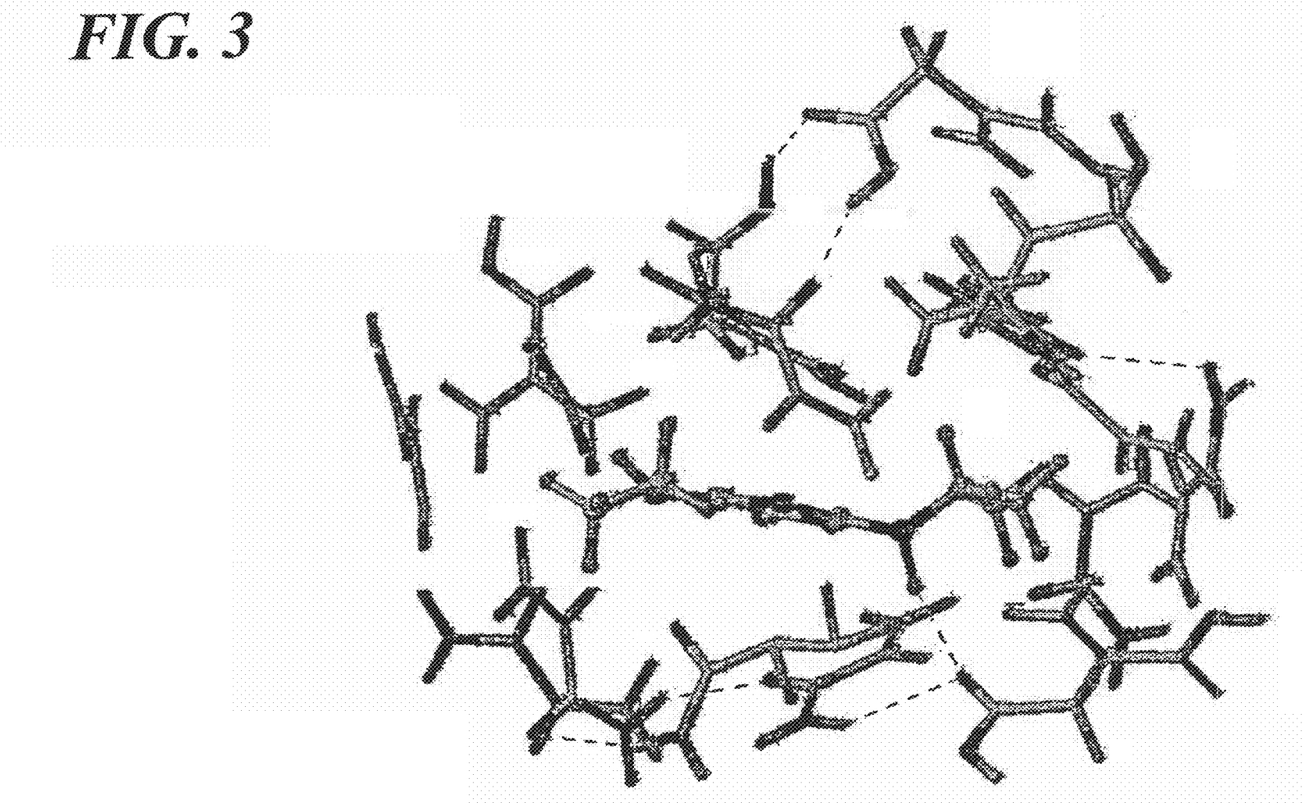
FIG. 3. Depicts interactions between functional monomers and atrazine in an optimized monomer-template complex.
Figure 4:
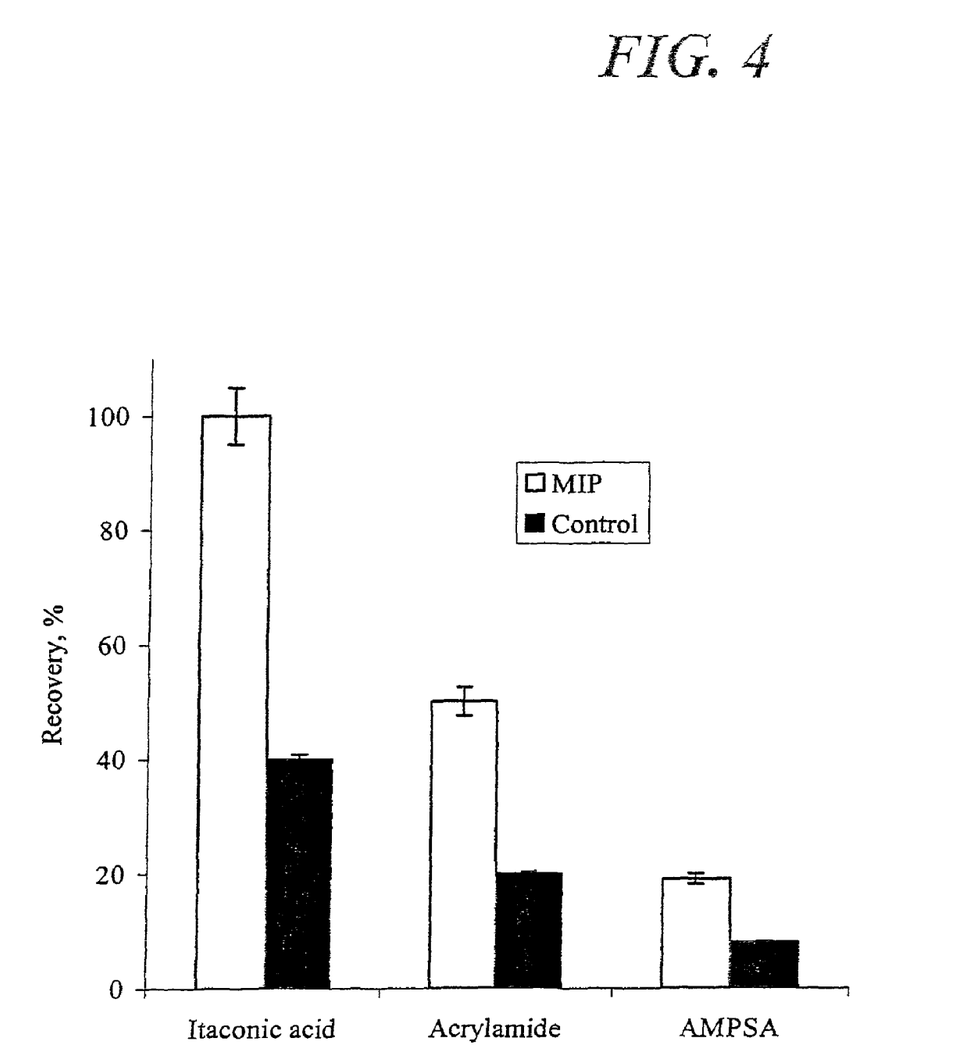
FIG. 4. Recovery of the atrazine by polymers, based on itaconic acid, acrylamide and AMPSA. 100 ml of herbicide solution in water ($10^{-9}$ M) were filtered through 100 mg of polymer and eluted with 90% methanol containing 10 mM HCl.

The LEAPFROG algorithm was used to analyze binding between monomers and template. 100,000 iterations were completed in approximately 8 hours, results from each run were examined and the empirical binding score was rank to the binding interactions between the functional monomers and atrazine. The best five are shown in FIG. 2. Their calculated binding scores were:

| | |
|---|---|
| Itaconic Acid | −37.05 kcal.mor$^{-1}$ |
| Acrylamide | −35.78 kcal.mor$^{-1}$ |
| 2-Acryl-2-methyl-1-propanesulphonic acid | −32.64 kcal.mol$^{-1}$ |
| N',N-Methylbisacrylate | −31.63 kcal.mol$^{-1}$ |
| Acrylic acid | −29.61 kcal.mol$^{-1}$ | b) The top three monomers (itaconic acid, acrylamide and 2-acryl-2-methyl-1-propanesulfonic acid) were next "packed" around the template using a salvation experiment. Simulated annealing was used to optimize the organization of the monomers around the template molecule. Annealing conditions were fixed as 1000K-10K. Equilibrium length was determined as 10000 ps. Energy minimization was performed to a 0.01 kcal mol$^{-1}$ convergence for each iteration. At the end of the program, the number and the position of the functional monomers were examined (FIG. 3). The type and quantity of the monomers participating in the complex with template indicate the type and ratio of the template and monomers in an optimized MIP composition. Accordingly to simulation atrazine forms in the model composition complex with 2 molecules of itaconic acid (first shell layer). The rest of the monomers are displaced from the complex as result of a competition process. At the same time, attention can also be paid to three molecules of acrylamide, which form a second shell layer interacting with itaconic acid from the first shell layer. The optimization of the MIP composition gives a template-monomers ratio 1 (atrazine):2 (itaconic acid):3 (acrylamide).

The calculated energy of the complex is based primarily on two figures: −29.0 kCal Mol$^{-1}$ for steric factors and −35.1 kCal Mol$^{-1}$ for electrostatic interactions.

c) The synthesis of polymers was made with solutions of corresponding monomers, as identified by computer simulation, using dimethylformamide as solvent and 80% cross-linker (ethyleneglycol dimethacrylate). Compositions are shown in Table 1.

TABLE 1

Composition of the computational polymers specific for atrazine.

| Polymer | Atrazine | Functional monomer | EGDM[1] | DMF[2] | Initiator[3] |
|---|---|---|---|---|---|
| AMPSA-MIP | 215 mg | 1044 mg AMPSA | 4 ml | 4 ml | 50 mg |
| AMPSA-Blank | — | 1044 mg AMPSA | 4 ml | 4 ml | 50 mg |
| AA-MIP | 215 mg | 284.32 mg AA | 2 ml | 2 ml | 50 mg |
| AA-Blank | — | 284.32 mg AA | 2 ml | 2 ml | 50 mg |
| IA-MIP | 215 mg | 520 mg IA | 3 ml | 3 ml | 50 mg |
| IA-Blank | — | 520 mg IA | 3 ml | 3 ml | 50 mg |

[1]EGDM—ethylene glycol dimethacrylate
[2]DMF—dimethylformamide
[3]1,1'-Azobis(cyclohexanecarbonitrile)

Figure 5:
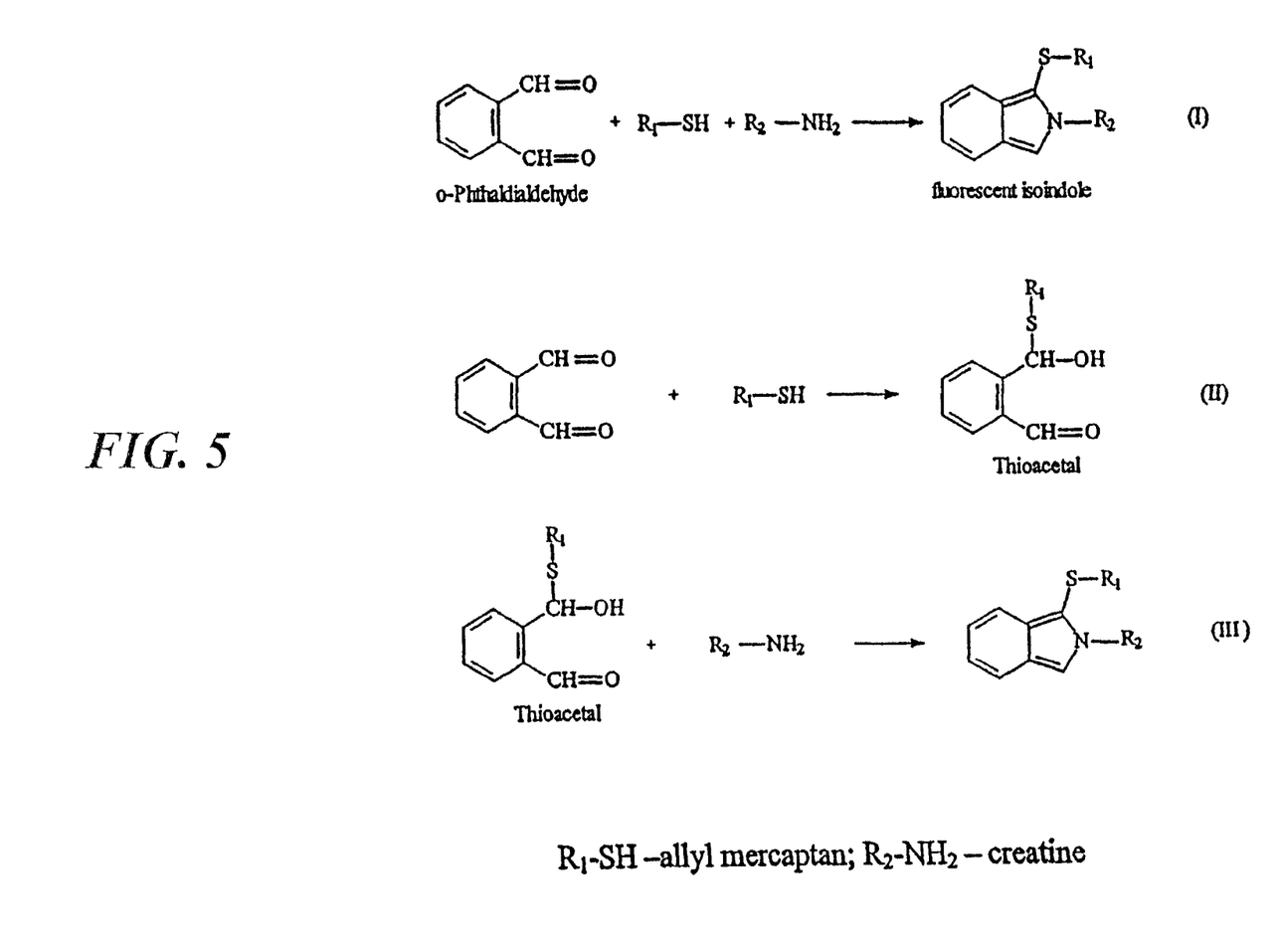
FIG. 5. Depicts interactions between functional monomers and methylated creatinine in an optimized monomer-template complex.

The polymerisation was initiated by adding 1% azobis (cyclohexane carbonitrile) and heating of the monomer mixture during 12 hours. The resulting polymer was ground, sieved and sedimented in acetone, giving a suspension with an average particle size of 45-106 µm. 100 ml of herbicide solution in water (10$^{-9}$ M) were filtered through 100 mg of polymer and eluted with 90% methanol containing 10 mM HCl. The herbicide concentration was measured using test-system based on the thylakoid membranes and Hill reaction (Piletskaya E. V. et al. (1999). *Anal. Chem. Acta,* 391, 1-7). A good correlation was found between the polymer affinity and the monomer binding score (FIG. 5). It was found that the MIPs designed using the computational approach had superior binding and recognition properties in comparison with a MIP designed using the conventional approach (based on methacrylic acid as a functional monomer). Additional polymer was prepared as described before using a template-monomers ratio 1 (atrazine):2 (itaconic acid):3 (acrylamide). This polymer has shown an atrazine binding similar to IA-based MIP with 100% efficiency of atrazine recovering (data not shown).

EXAMPLE 2

Computer Aided Design of the MIP Specific for Creatinine a) The virtual library used for the design of an MIP specific for creatinine contained 20 monomers as used in Example 1 and one additional monomer—polymerizable thioacetal formed by allyl mercaptan and o-phthalic dialdehyde, which was necessary for creatinine sensing. Creatinine analogue—N,N'-dimethylcreatinine was used as a template instead of creatinine in order to prevent covalent interactions between the template and the functional monomers. The computer simulation was performed in the same way as described in Example 1. The optimized composition contains template-monomers ratio 1 (N,N'-dimethylcreatinine):3 (thioacetal):1 (urocanic ethyl ester) (FIG. 5).

b) Three polymers were synthesized using a conventional selection of monomers (with cross-linker only and with methacrylic as functional monomer) and computational selection. Three additional blank polymers were prepared in the absence of template. The composition of the monomer mixtures is shown in Table 2.

O-phthalic dialdehyde (563 mg) and allyl mercaptan (330 mg) were dissolved in 2 ml of DMSO and mixed with methylated creatinine (131 mg). Functional monomers, methacrylic acid (258 mg) (MIP B) or urocanic acid ethyl ester (138 mg) (MIP C) and azobis (cyclohexane carbonitrile) (ACC) (50 mg) were added to the monomers, the solution was purged with nitrogen and left for 1 hour at room temperature. The polymerization was initiated by heating overnight at 80° C. The resulting polymer was ground, sieved and sedimented in acetone, giving a suspension with an average particle size of 5 µm. Three additional blank polymers were prepared in the absence of template.

TABLE 2

Composition of polymers designed using conventional and computational approaches

| Polymer | AM | OPA | MA | Urocanic acid ethyl ester | Creatinine |
|---|---|---|---|---|---|
| MIP A | 330 ul (µmol) | 563 mg (µmol) | — | — | 113 mg (µmol) |
| Blank A | 330 ul (µmol) | 563 mg (µmol) | — | — | — |
| MIP B | 330 ul (µmol) | 563 mg (µmol) | 258 ul µmol) | — | 113 mg (µmol) |
| Blank B | 330 ul (µmol) | 563 mg (µmol) | 258 ul (µmol) | — | — |
| MIP C | 330 ul (µmol) | 563 mg (µmol) | — | 138.13 mg (µmol) | 113 mg (µmol) |
| Blank C | 330 ul (µmol) | 563 mg (µmol) | — | 138.13 mg (µmol) | — |

Figure 6:
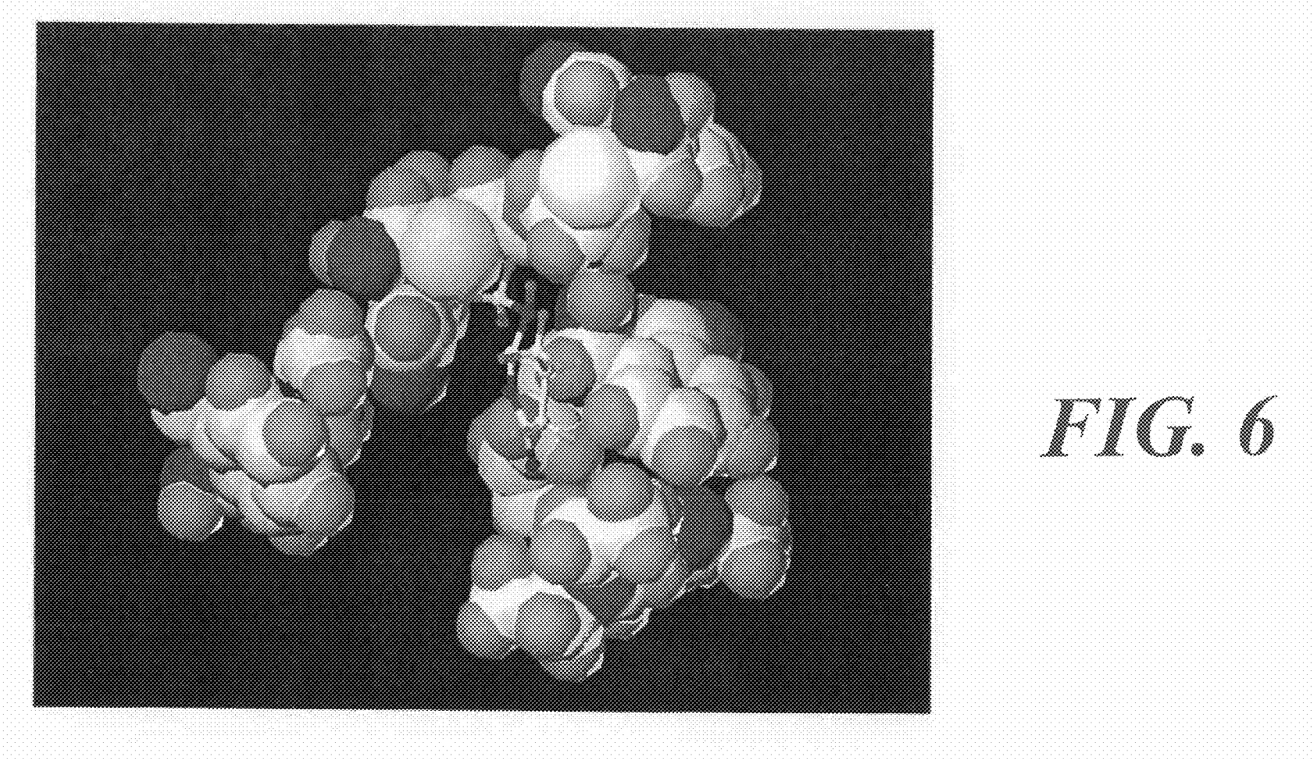
FIG. 6. Interaction between phthalic dialdehyde, mercaptan group (OPA reagents) and primary amine (I); thioacetal formation (II); formation of fluorescent complex between thioacetal and primary amine (III).
Figure 7:
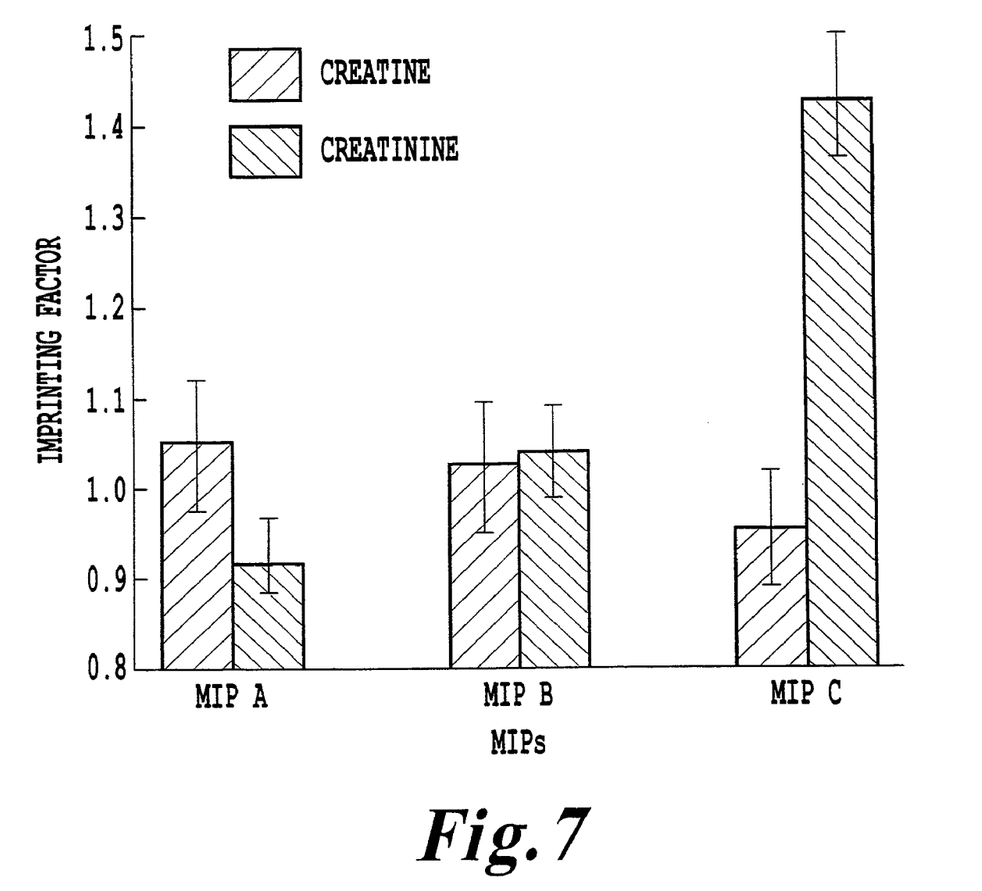
FIG. 7. Depicts imprinting factors of the polymers MIP A, MIP B and MIP C calculated for creatinine and creatine. Imprinted factors were calculated using equation $I=\Delta F(MIP)/\Delta F(Blank)$ where $\Delta F$ is change in fluorescence for MIP and blank polymers, correspondingly. Measurements were made in 100 mM sodium phosphate buffer, pH 7.0 (Ex=320 nm; Em=410 nm).

AM—allyl mercaptan
OPA—o-phtalic dialdehyde;
MA—methacrylic acid;
All the monomer mixtures contained 2 ml of EDMA—ethylene glycol dimethylacrylate and 2 ml of DMSO—dimethyl sulfoxide with 50 mg of AIBN—azobis(isobutyronitrile).

c) Polymer recognition properties were analyzed by measuring fluorescence changes generated by a polymer suspension following the reaction between primary amines and polymer thioacetal leading to formation of an isoindole complex (FIG. 6). The imprinting factor, calculated for MIPs, clearly indicates the superior selectivity of the polymer designed using the computational approach in comparison with polymers designed using a traditional approach (FIG. 7).

The invention claimed is:

1. A process for computer aided rational molecular design of a molecularly imprinted polymer, comprising:
with the aid of a computer in each of the following steps:
establishing a virtual library of molecular models of functional monomers each having a polymerizable group and a functional group, wherein the functional group is capable of interacting with a template molecule;
designing a molecular model of the template molecule by a computer facilitated molecular mechanical method;
screening the virtual library of molecular models of functional monomers according to a binding score, wherein the binding score of each molecular model of the functional monomers is determined between the molecular model of the functional monomer and the molecular model of the template molecule, to identify a group A of monomers which have the highest binding scores to the molecular model of the template molecule;
simulating, by molecular mechanics, a prearrangement of the group A of monomers with the molecular model of the template molecule to determine the number of the monomers of the group A of functional monomers and position of the monomers of the group A of functional monomers around the template molecule;
indicating a synthesis composition to make the molecularly imprinted polymer by the identity of the functional monomers of the group of monomers A and the quantity of the functional monomers of the group of monomers A; and
synthesizing the molecularly imprinted polymer by polymerizing the synthesis composition.

2. The process as claimed in claim 1, wherein the simulating identifies the number of each of the monomers of the group A of monomers relative to one molecule of the molecular model of the template molecule.

3. The process as claimed in claim 1, wherein the screening identifies whether the group A of monomers has a higher binding score when the group A contains a mixture of different functional monomers.

4. The process of claim 1, wherein the template molecule is selected from the group consisting of a biological receptor, a nucleic acid, an immunosuppressant, a hormone, a heparin, an antibiotic, a vitamin, a drug, a synthetic molecule possessing biological activity, a cell component, a component of virus, a carbohydrate, a lipid, a saccharide, a nucleoprotein, a mucoprotein, a lipoprotein, a peptide, a protein, a glycoprotein, a glucosaminoglycane and a steroid.

5. The process of claim 1, wherein the group A of monomers comprises at least two monomers each having at least one functional group capable of interacting with the template molecule through one or more of an electrostatic bond, a van-der-Waals force, a dipole-dipole interaction and a reversible covalent bond,
wherein the monomers of the group A of monomers is selected from the group consisting of a vinyl monomer, an allyl monomer, an acetylene, an acrylate, a methacrylate, an amino acid, a nucleoside, a nucleotide, a carbohydrate, a phenol, a heterocycle, an aniline compound, and mixtures thereof.

6. The process as claimed in claim 1, wherein the template molecule is a biological template molecule selected from the group consisting of a biological receptor, a nucleic acid, an immunosuppressant, a hormone, a heparin, an antibiotic, a vitamin, a synthetic molecule possessing biological activity, a cell component, a component of a virus, a carbohydrate, a lipid, a saccharide, a nucleoprotein, a mucoprotein, a lipoprotein, a peptide, a protein, a glycoprotein, a glucosaminoglycane and a steroid.

7. The process as claimed in claim 1, wherein the binding score is the dissociation constant between the molecular model of the functional monomer and the molecular model of the template molecule.

8. The process as claimed in claim 1, wherein the synthesis composition is polymerized in the absence of the template molecule to form the molecularly imprinted polymer.

* * * * *